(12) United States Patent
Choi et al.

(10) Patent No.: US 9,282,620 B2
(45) Date of Patent: Mar. 8, 2016

(54) APPARATUS AND METHOD FOR GENERATING CONSTANT CURRENT PULSE WAVE, MEDICAL OPERATION METHOD USING SAME, AND LIGHT GENERATING APPARATUS

(75) Inventors: Hak Ki Choi, Seoul (KR); Kwang Chon Ko, Paju-Si (KR)

(73) Assignee: Lutronic Corporation, Gyeonggi-do (KR)

( * ) Notice: Subject to any disclaimer, the term of this patent is extended or adjusted under 35 U.S.C. 154(b) by 755 days.

(21) Appl. No.: 13/394,887

(22) PCT Filed: Sep. 13, 2010

(86) PCT No.: PCT/KR2010/006221
§ 371 (c)(1),
(2), (4) Date: Mar. 8, 2012

(87) PCT Pub. No.: WO2011/031110
PCT Pub. Date: Mar. 17, 2011

(65) Prior Publication Data
US 2012/0172950 A1    Jul. 5, 2012

(30) Foreign Application Priority Data

Sep. 11, 2009  (KR) .......................... 10-2009-0085662

(51) Int. Cl.
*H05B 37/02* (2006.01)
*H05B 41/34* (2006.01)
(Continued)

(52) U.S. Cl.
CPC ................ *H05B 41/34* (2013.01); *A61B 18/20* (2013.01); *H05B 37/02* (2013.01); *A61B 2017/00159* (2013.01); *A61B 2017/00172* (2013.01)

(58) Field of Classification Search
CPC .......... H05B 37/00; H05B 37/02; H05B 41/30
USPC ....... 315/194, 200 A, 219, 224, 241 P, 241 S, 315/291, 307, 308
See application file for complete search history.

(56) References Cited

U.S. PATENT DOCUMENTS 4,942,340 A * 7/1990 Ikawa ......................... 315/241 P
5,680,017 A * 10/1997 Veldman et al. .............. 315/308
(Continued)

FOREIGN PATENT DOCUMENTS

JP   2003-197556 A   7/2003
JP   2006-108128 A   4/2006
(Continued)

OTHER PUBLICATIONS

International Search Report w/translation from PCT/KR2010/006221 dated May 27, 2011 (6 pages).
(Continued)

*Primary Examiner* — Tung X Le
(74) *Attorney, Agent, or Firm* — Osha Liang LLP

(57) ABSTRACT

Disclosed are an apparatus and a method for generating a constant current pulse wave, a medical operation method using the same, and a light generating apparatus. The apparatus for generating a constant current pulse wave comprises: a charge unit receiving a current and charging electric charges; a converter unit applying a constant voltage to a flash lamp during a first reference time and applying a constant current to the flash lamp during a second reference time by using the electric charges charged in the charge unit; and a controller operating in a constant voltage control mode to transmit a constant voltage control signal for controlling the converter unit to output the constant voltage, to the converter unit during the first reference time and operating in a constant current control mode to transmit a constant current control signal for controlling the converter unit to output the constant current, to the converter unit during the second reference time. Accordingly, a stable pulse wave of the constant current can be applied to the flash lamp.

15 Claims, 9 Drawing Sheets

(51) Int. Cl.
*A61B 18/20* (2006.01)
*A61B 17/00* (2006.01)

(56) References Cited

U.S. PATENT DOCUMENTS

| | | | | |
|---|---|---|---|---|
| 6,066,926 | A * | 5/2000 | Yamada | H05B 41/32 315/241 P |
| 6,453,145 | B1 * | 9/2002 | Miura | 399/336 |
| 7,375,471 | B2 * | 5/2008 | Matsumura | H02M 3/33507 315/200 A |

FOREIGN PATENT DOCUMENTS

| KR | 2001-0036749 A | 5/2001 |
|---|---|---|
| KR | 10-0554223 B1 | 3/2006 |
| KR | 10-2006-0127368 A | 12/2006 |

OTHER PUBLICATIONS

Patent Abstracts of Japan Publication No. 2003-197556 dated Jul. 11, 2003 (1 page).
Korean Patent Abstract Publication No. 1020060127368 dated Dec. 12, 2006 (2 pages).
Korean Patent Abstract Registration No. 100554223 dated Feb. 15, 2006 (2 pages).
Patent Abstracts of Japan Publication No. 2006-108128 dated Apr. 20, 2006 (1 page).
Korean Patent Abstract Publication No. 1020010036749 dated May 7, 2001 (2 pages).

* cited by examiner

APPARATUS AND METHOD FOR GENERATING CONSTANT CURRENT PULSE WAVE, MEDICAL OPERATION METHOD USING SAME, AND LIGHT GENERATING APPARATUS

TECHNICAL FIELD

The present invention relates to an apparatus and method for generating a constant current pulse wave, a medical operation method using the same, and a light generating apparatus and, more particularly, to a technique of generating a constant current pulse wave to discharge a flash lamp capable of generating uniform optical power, e.g., a laser output, or the like, by applying a square pulse of a constant current to a flash lamp of a high voltage and high current during a reference frame time.

BACKGROUND ART

Recently, medical operation methods using light such as a laser, an intensed pulsed light (IPL), visible ray, infrared ray, and the like, have been rapidly spreading. For example, in the past, a medical operation method using light was mostly applied to a surgical operation, or the like, but recently, it is applied to various fields such as a plastic surgery, an operation for skin care, and the like.

In general, in order to oscillate a laser, laser oscillation medium is used. The laser oscillation medium may be made of, for example, Nd:YAG, Ruby, $CO_2$, He, Ne, or the like, and may have a rod shape, or the like.

As an energy transmission device for exciting the laser oscillation medium, a high voltage/high current flash lamp charged with a discharge gas such as xenon, krypton, or the like, is commonly used, and an energy level of a laser generation can be obtained by exciting the laser generation medium by optical energy according to discharging of the flash lamp.

The size of the laser energy generated by the laser oscillation medium is dependent upon the size of the optical energy transferred from the flash lamp as an exciplex (or an excimer), and a period of time during which a laser is generated is also dependent upon an optical energy transfer period of the flash lamp.

Thus, in order to obtain a laser output having a certain size during a relatively long period of time, e.g., for tens of milliseconds (which is denoted simply by 'mS' in the present disclosure), the intensity of optical energy transferred from the flash lamp is required to be uniform, and in order to make the intensity of optical energy of the flash lamp discharged to the laser oscillation medium uniform, a current amount flowing through the flash lamp is required to be uniform.

FIG. 1 is a circuit diagram showing a configuration of the related art general flash lamp discharge driving apparatus, which briefly illustrates the configuration of the general flash lamp discharge driving apparatus disclosed in U.S. Pat. No. 5,620,478, for example, in FIG. 19, or the like. FIG. 2 is a graph showing current and voltage characteristics of an energy charging capacitor C illustrated in FIG. 1 when the energy charging capacitor C is discharged.

As shown in FIG. 1, when DC charge power is applied to the energy charging capacitor C, high level electric charges are charged and stored in the energy charging capacitor C. Thereafter, when the electric charges charged in the energy charging capacitor C are discharged to the flash lamp L, the flash lamp L is discharged and light is irradiated to a laser oscillation medium or a skin.

In this case, as shown in FIG. 2, a discharge current and the voltage of the energy charging capacitor C are reduced inverse-exponential functionally, and here, optical power discharged from the flash lamp L also has characteristics that it is reduced in a manner similar to that of the current/voltage characteristics illustrated in FIG. 2. Thus, when the flash lamp L is discharged by using the related art flash lamp discharge driving apparatus, since the output from the flash lamp L is inverse-exponential functionally reduced, resulting in a failure to generate optical power having a uniform size.

Thus, when uniform optical power is not generated from the flash lamp, in general, excessive energy is applied at an initial stage and dwindling energy is applied over the lapse of time. Thus, it is highly likely to irradiate a larger or smaller amount of laser than required to the affected part such as a patient's skin, or the like.

However, when an excessive amount of laser is irradiated to the affected part, a side effect such as a burn, or the like, may be generated, and conversely, if a smaller amount of laser is irradiated to the affected part, a treatment effect is insufficient. Thus, a technique of uniformly maintaining optical power of a laser for a particular period of time is urgently required.

Meanwhile, besides the method of generating and using a laser for a treatment by using a flash lamp and a laser oscillation medium as mentioned above, a medical treatment method using a device which is so-called IPL has been known.

The treatment method using IPL will be briefly described. Unlike the laser treatment method, a filter allowing only a particular wavelength to pass therethrough is provided near a flash lamp, and natural light such as visible light, infrared ray, ultraviolet ray, or the like, is allowed to pass through the filter so as to be directly irradiated to the skin for a treatment.

Like the treatment method using a laser, in the treatment method using IPL, the size of energy of light irradiated to the skin must be uniform, for which, thus, the current amount flowing through the flash lamp L must be uniform. In particular, in case of IPL, the flash lamp has characteristics in which a wavelength spectrum of emitted optical power is varied according to the size of a discharged current. Thus, when IPL is applied to a treatment method for which a particular wavelength is to be selected for the purpose of treating certain lesion, stable optical power is required.

Thus, when a surgical procedure is performed on the affected part such as a surface of a patient's skin, or the like, by using a laser, an IPL device, or the like, for a treatment, development of a basic technique of irradiating light of uniform optical power for a particular time is urgently required.

DISCLOSURE

Technical Problem

Therefore, an aspect of the present invention provides an apparatus and method for generating a constant current pulse wave capable of supplying uniform energy to a flash light by performing constant voltage controlling to uniformly maintain a voltage during a first reference time (e.g., for a certain time starting from a frame initiation timing) and performing constant current controlling to uniformly maintain a current during a second reference time (e.g., until a frame termination timing after a first time), a medical operation method using the same, and a light generating apparatus.

Technical Solution

According to an aspect of the present invention, there is provided an apparatus for generating a constant current pulse wave. The apparatus for generating a constant current pulse wave includes: a charge unit receiving a current and charging electric charges; a converter unit applying a constant voltage to a flash lamp during a first reference time and applying a constant current to the flash lamp during a second reference time by using the electric charges charged in the charge unit; and a controller operating in a constant voltage control mode to transmit a constant voltage control signal for controlling the converter unit to output the constant voltage, to the converter unit during the first reference time and operating in a constant current control mode to transmit a constant current control signal for controlling the converter unit to output the constant current, to the converter unit during the second reference time. The second reference time may be a period of time until a point in time at which a reference frame terminates after the first reference time expires.

The apparatus may further include: an output voltage detection unit detection an output voltage of the converter unit; and an output current detection unit detection a current output from the converter unit.

The controller may include: a constant voltage output controller operating during the first reference time, comparing the output voltage of the converter unit detected by the output voltage detection unit with a pre-set reference voltage value used for controlling a constant voltage, and outputting a constant voltage output control signal for controlling the converter unit to output the constant voltage, to the converter unit based on the comparison voltage value; and a constant current output controller operating during the second reference time, comparing the output current of the converter unit detected by the output current detection unit with a pre-set reference current value used for controlling a constant current, and outputting a constant current output control signal for controlling the converter unit to output the constant current, to the converter unit based on the comparison current value.

The apparatus may further include: a reference current value generation unit storing the current value detected by the output current detection unit during the first reference time, as the reference current value used for controlling a constant current. When the reference frame terminates, the reference current value generation unit may extinguish the stored reference current value used for controlling a constant current.

The apparatus may further include: a third switching unit outputting a signal for controlling the reference current value generation unit to extinguish the stored reference current value used for controlling a constant current, to the current value generation unit, when the reference frame terminates; and a reference frame timer outputting a control signal for operating the third switching unit at a point in time at which the reference frame terminates, to the third switching unit.

The apparatus may further include: a first switching unit outputting a signal for turning off an operation of the constant voltage output controller to the constant voltage output controller when the first reference time expires; and a second switching unit outputting a signal for turning on an operation of the constant current output controller during the second reference time, to the constant current output controller.

The apparatus may further include: a converter ON/OFF controller turning on the converter unit by a read-in signal input to a signal input unit to charge the converter unit with a constant voltage output voltage, controlling an ON/OFF operation of the converter unit by a pumping pulse input to a pumping pulse input terminal of the signal input unit, turning on the converter unit during a pulse period in case of a pumping operation by divided pulses, and turning off the converter unit during a pulse idle period; and an output pulse switch unit connected to an output terminal and synchronized with a pumping pulse input to perform an ON/OFF operation to allow a voltage of an energy level sufficient to allow a pumping current of a constant current to flow in an output smoothing condenser provided in the converter unit even when the converter unit is in an OFF state.

The apparatus may further include: a reverse pulse removing unit removing a reverse impulse voltage generated as soon as an output pulse switch is turned off; a simmer back flow preventing unit preventing a simmer current, which is being supplied to both ends of the flash lamp, from flowing backward; an output line regulating unit interrupting a high trigger voltage applied to the flash lamp so as to be ignited into a simmer state, and changing it into an ON state; a residual electric charge discharge unit discharging electric charges remaining in a discharge energy charge unit and the output smoothing condenser provided in the converter unit when the supply power is turned off; an output voltage discharge unit discharging a voltage of the output smoothing condenser provided in the converter unit to reach an output voltage required by a low level set again in order to prevent generation of a possibility of discharging excessive energy when a low level value is selected without discharging energy after an energy level is set; and a reference voltage floating conversion unit performing DC conversion on a reference voltage value input to a reference voltage value input terminal of a signal conversion unit after being referenced to a ground and outputting the same to the controller to allow the controller to compare the reference voltage value with an output voltage of the converter unit to perform constant voltage output controlling.

According to another aspect of the present invention, there is provided an apparatus for generating a constant current pulse wave. The apparatus for generating a constant current pulse wave includes: a charge unit receiving a current and charging electric charges; a converter unit applying a constant voltage to a flash lamp during a first reference time and applying a constant current to the flash lamp during a second reference time by using the electric charges charged in the charge unit; a constant voltage output controller detection an output voltage of the converter unit and applying a constant voltage control signal for controlling the converter unit to output the constant voltage, to the converter unit based on the detected output voltage and a pre-set reference voltage; and a constant current output controller detection an output current of the converter unit and applying a constant current control signal for controlling the converter unit to output the constant current, to the converter unit based on the detected output current and a pre-set reference current.

The apparatus may further include: an output voltage detection unit detection an output voltage of the converter unit; a reference current value generation unit storing the current value detected by the output current detection unit during the first reference time, as a reference current value used for controlling a constant current; and an output current detection unit detection a current output from the converter unit.

According to another aspect of the present invention, there is provided a method for generating a constant current pulse wave. The method for generating a constant current pulse wave using an apparatus for generating a constant current pulse wave, includes receiving a current and storing electric charges in a charge unit; performing a constant voltage output mode to perform constant voltage controlling by using the stored electric charges and output a constant voltage to a flash lamp during a first reference time; and performing a constant current output mode to perform constant current controlling by using the stored electric charges to output a constant current to the flash lamp during a second reference time until when a reference frame terminates after the first reference time expires.

The performing of the constant voltage output mode may include: detection an output voltage of a converter unit; comparing the detected output voltage of the converter unit with a pre-set reference voltage value to calculate a comparison voltage value; and controlling the converter unit to output the constant voltage, based on the comparison voltage value.

The performing of the constant current output mode may include: detection an output current of the converter unit; comparing the detected output current of the converter unit with a predetermined reference current value to calculate a comparison current value; and controlling the converter unit to output the constant current, based on the comparison current value.

The method may further include: detection an output current of the converter unit during the first reference time; and storing the output current of the converter unit detected during the first reference time, as a reference current value used for controlling the constant current. Also, the method may further include: extinguishing the stored reference current value used for controlling the constant current when the reference frame termination timing arrives.

According to another aspect of the present invention, there is provided a medical operation method using an apparatus for generating a constant current pulse wave. In the medical operation method, a constant current pulse wave is supplied to a flash lamp by using a constant current pulse wave generating apparatus which receives a current and charges electric charges, outputs a constant voltage during a first reference time by using the charged electric charges, and outputs a constant current during a second reference time until when a reference frame terminates after the first reference time expires, and light for a treatment is irradiated to the affected part by using a light generating apparatus which generates light for a treatment based on optical energy generated from the flash lamp.

According to another aspect of the present invention, there is provided a light generating apparatus. The light generating apparatus includes: a constant current pulse wave generating apparatus receiving a current and charging electric charges, outputting a constant voltage during a first reference time by using the charged electric charges, and outputting a constant current during a second reference time until when a reference frame terminates after the first reference time expires; and a flash lamp generating optical energy by using a constant current pulse wave applied from the constant current pulse wave generating apparatus, wherein light for a treatment is generated based on optical energy output from the flash lamp.

Advantageous Effects

According to embodiments of the present invention, based on the technique of generating a constant current pulse wave according to embodiments of the present invention, a controlling operation of uniformly maintaining a voltage is performed during a first certain period of time and a controlling operation of uniformly maintaining a current is performed during a next period of time, thereby allowing a uniform current to flow through the flash lamp. For example, according to embodiments of the present invention, in a laser generating apparatus or IPL, a flash lamp is able to output a uniform constant current of a long pulse (tens of mS to hundreds of mS) in the form of a high current (some 100 A to some 1000 A). Thus, an effect of obtaining a laser output or optical power maintaining an intended certain size during a treatment time of a relatively long pulse (a few mS to hundreds of mS) can be obtained.

Also, with respect to a current discharged from the flash lamp L, a single wave of a long pulse period or a pulse wave divided into a plurality of divided pulses is formed and adjusted by a certain time width to implement a square pulse wave having a certain width and having that characteristics that a rising time and a falling time of a flash lamp discharge current are very fast, and as a result, an energy output value (laser output or optical power) having a certain size can be quickly (immediately) obtained.

In addition, since a reference voltage value for controlling a constant voltage can be variably input through a signal input unit and a DC/DC converter is able to output a constant current to the flash lamp according to the input reference voltage value, whereby a user can freely set and control an energy level (current value) desired to be output.

BEST MODES

Hereinafter, embodiments will be described in detail with reference to the accompanying drawings such that they can be easily understood by those skilled in the art to which the present invention pertains. In the embodiments of the present invention described hereinafter, particular technical terms are used to clarify content. However, it should be appreciated that each of the particular terms is not limited to the selected particular term but include all the technical equivalents operating in a similar manner to achieve similar objects.

Figure 1:
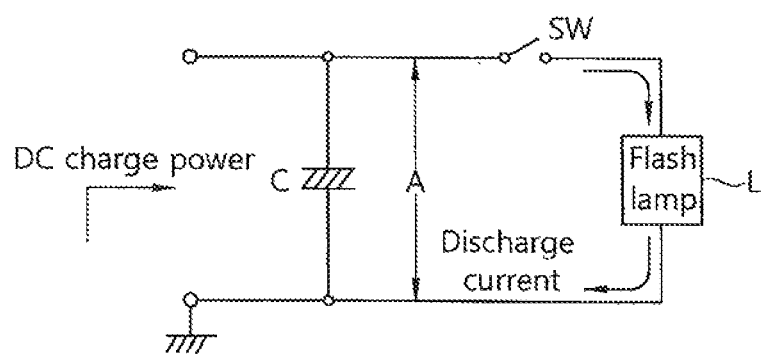
FIG. 1 is a circuit diagram illustrating a configuration of the related art general flash lamp discharge driving apparatus.
Figure 2:
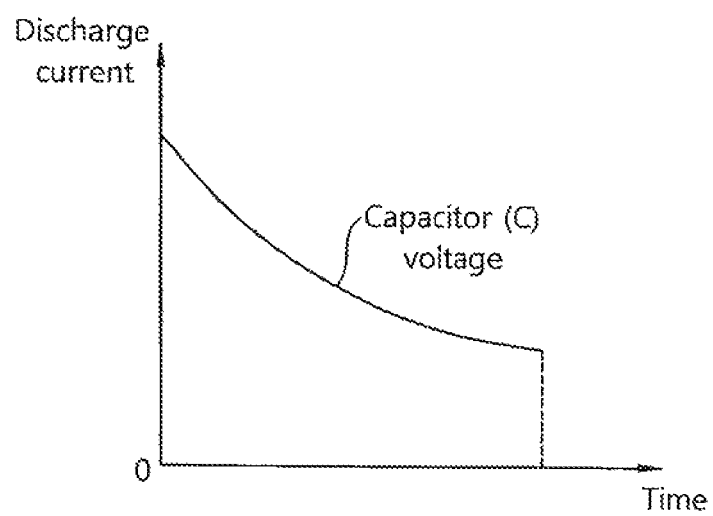
FIG. 2 is a graph showing current and voltage characteristics of an energy charging capacitor illustrated in FIG. 1 when the energy charging capacitor is discharge.
Figure 3:
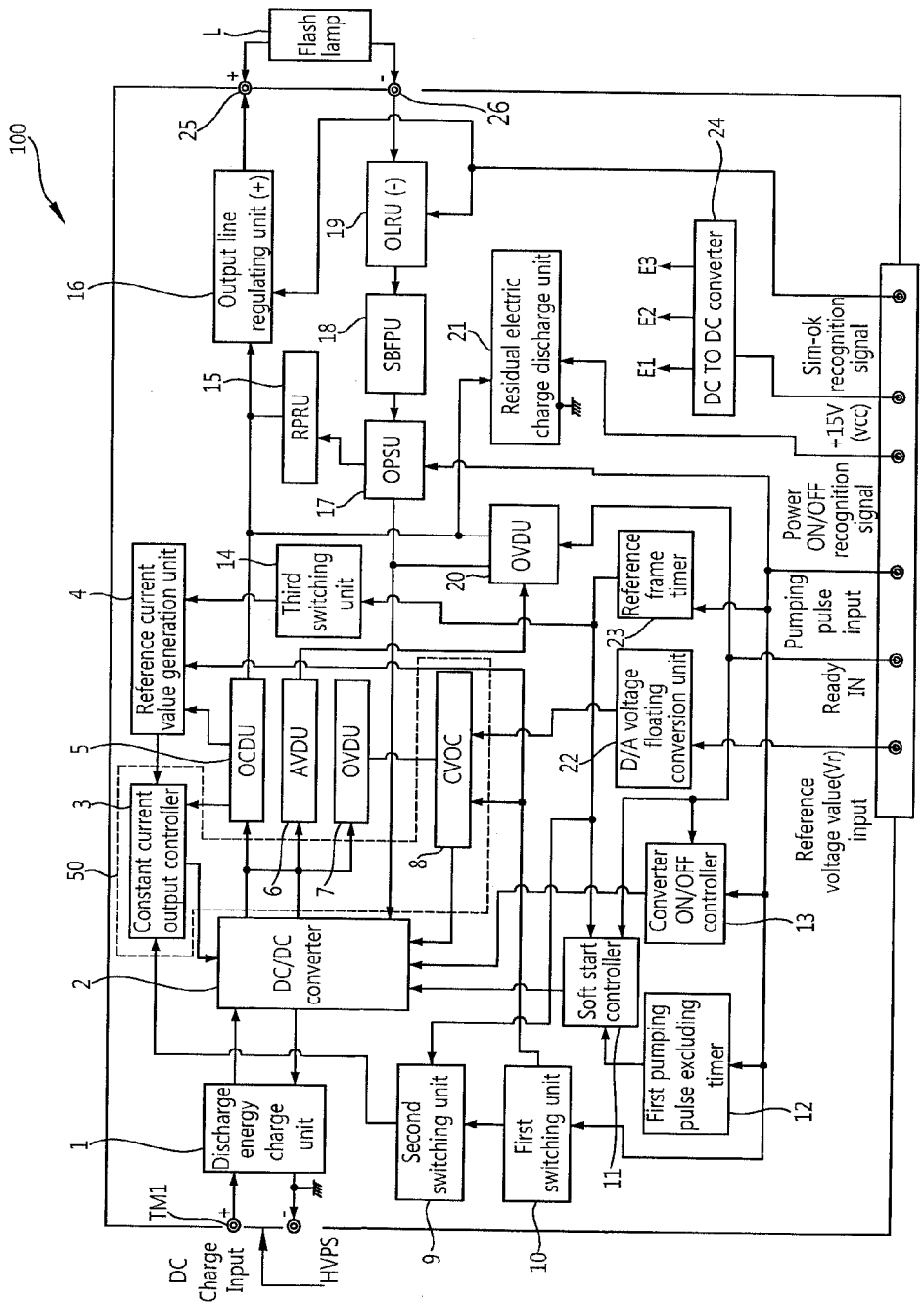
FIG. 3 is a schematic block diagram illustrating a configuration of an apparatus for generating a constant current pulse wave according to an embodiment of the present invention.
Figure 4:
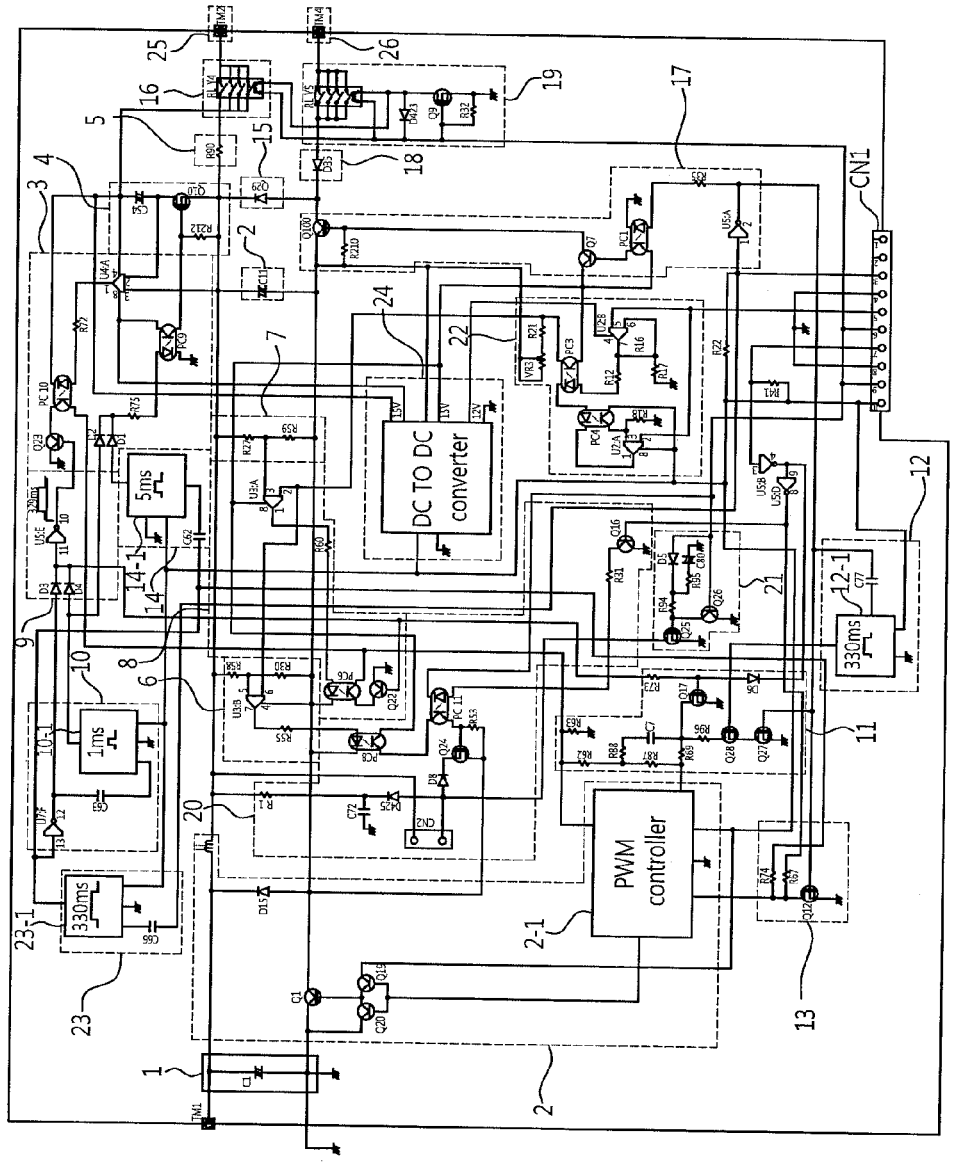
FIG. 4 is a circuit diagram illustrating a circuit configuration of the apparatus for generating a constant current pulse wave according to an embodiment of the present invention.

FIG. 3 is a schematic block diagram illustrating a configuration of an apparatus for generating a constant current pulse wave according to an embodiment of the present invention. FIG. 4 is a circuit diagram illustrating a circuit configuration of the apparatus for generating a constant current pulse wave according to an embodiment of the present invention.

As shown in FIGS. 3 and 4, the apparatus 100 for generating a constant current pulse wave (will be referred to as a 'constant current pulse wave generating apparatus 100', hereinafter) according to an embodiment of the present invention may include a discharge energy charge unit 1, a DC/DC converter 2, a controller 50, an output voltage detection unit 7, a reference current value generation unit 4, an output current detection unit 5, a first switching unit 10, a second switching unit 9, a third switching unit 14, a reference frame timer 23, an output voltage discharge unit 20, a residual electric charge discharge unit 21, an abnormal voltage detection unit 6, a converter ON/OFF controller 13, a soft start controller 11, a first pumping pulse excluding timer 12, a reverse pulse removing unit 15, an output line regulating unit (+) 16, an output pulse switch unit 17, a simmer back flow preventing unit 18, an output line regulating unit (+) 19, a D/A voltage floating conversion unit 22, a DC to DC converter 24, and the like.

The discharge energy charge unit 1 may refer to an energy storage unit for receiving an applied current, e.g., a DC current, storing electric charges, and discharging the charged electric charges. The discharge energy charge unit 1 may be configured as an energy charging capacitor C1 having a very great capacitance value. When electric charges in the discharge energy charge unit 1 are discharged, a terminal voltage is dropped.

The DC/DC converter 2 may charge the electric charges discharged from the discharge energy charge unit 1 therein, apply a constant voltage to the flash lamp L under the control of the constant voltage output controller 8 during a first reference time T1 by using the charged electric charges, and output a constant current to the flash lamp L under the control of the constant current output controller 3 during a second reference time T2.

In order to perform such functions, preferably, the DC/DC converter 2 may be comprised of a PWM controller 2-1, switching elements Q1, Q2, and Q3 connected to an output terminal of the PWM controller 2-1, a free wheel diode D15, an inductor L1, an output smoothing condenser C11, and the like.

The first reference time T1 may refer to a period of time starting from an initiation of a reference frame to a predetermined timing. Here, the reference frame may refer to a process in which the energy charging capacitor 1 in a fully-charged state starts discharging and then reaches an intended certain voltage (energy). For example, the reference frame may be one frame.

Thus, the first reference time T1 may be a period of time from a point in time at which the energy charging capacitor 1 starts discharging to a particular point in time. For example, the first reference time T may be set to be 1 mS, or the like, and in the present embodiment, the first reference time T1 is assumed to be 1 mS. However, the present invention is not limited thereto and the first reference time may be variably set according to an implementation environment.

The first reference time T1 may refer to a period of time during which the constant current pulse wave generating apparatus 100 operates in a constant voltage output mode, starting from point in time at which a reference frame is initiated. When the first reference time T1 has lapsed, the constant current pulse wave generating apparatus 100 changes from the constant voltage output mode to a constant current output mode.

The second reference time T2 may refer to a period of time starting from a point of time at which the first reference time T1 has passed to a point in time at which the reference frame terminates. Namely, the second reference time T2 may be a period of time during which the constant current pulse wave generating apparatus 100 operates in the constant current output mode.

The constant voltage output mode may refer to a mode in which the constant current pulse wave generating apparatus 100 outputs a constant voltage to the flash lamp L. The constant current output mode may refer to a mode in which the constant current pulse wave generating apparatus 100 outputs a constant current to the flash lamp L.

The controller 50 may perform a function of operating in the constant voltage control mode to transmit a constant voltage control signal to the DC/DC converter 2 to allow the DC/DC converter 2 to output a constant voltage during the first reference time, and operating in the constant current control mode to transmit a constant current control signal to the DC/DC converter 2 to allow the DC/DC converter 2 to output a constant current during the second reference time. Namely, the controller 50 operates in the constant voltage control mode in the constant voltage output mode, and operates in the constant current control mode in the constant current output mode. The controller 50 may include the constant voltage output controller 8 and the constant current output controller 3. Functions of these elements will be described in detail later.

Figure 5:
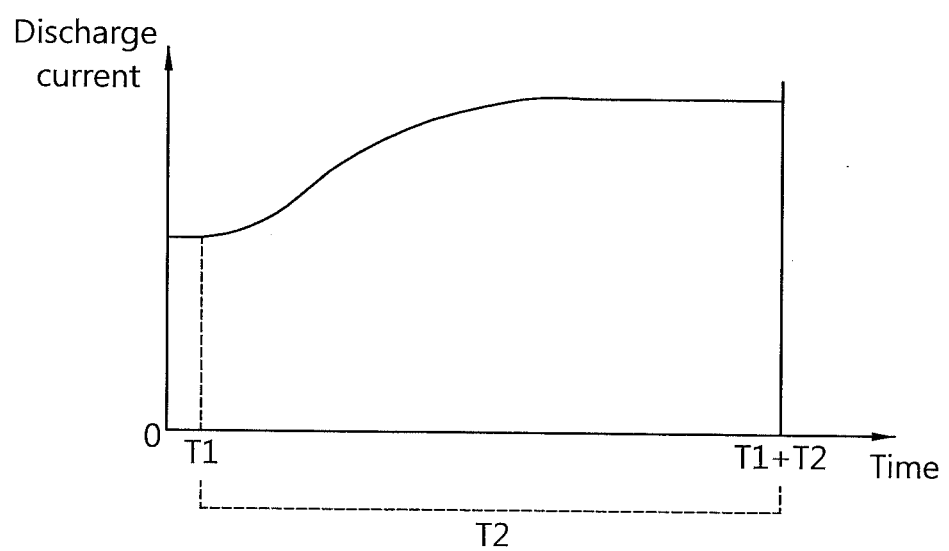
FIG. 5 is a graph explaining a waveform of a discharge current in a general constant voltage controlling operation.
Figure 6:
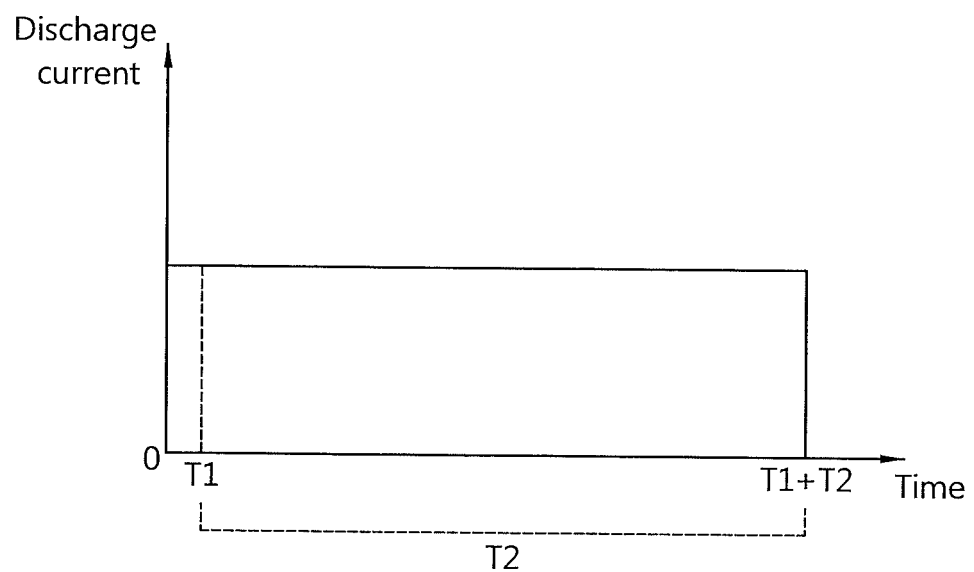
FIG. 6 is a graph showing a waveform of a discharge current when constant voltage controlling and constant current controlling are performed according to an embodiment of the present invention.

FIG. 5 is a graph explaining a waveform of a discharge current in a general constant voltage controlling operation, and FIG. 6 is a graph showing a waveform of a discharge current when constant voltage controlling and constant current controlling are performed according to an embodiment of the present invention.

As illustrated in FIG. 5, in general, when a uniform constant voltage is applied to the flash lamp L, after a certain time has lapsed, a discharge current assumes an aspect of being increased.

In comparison, in an embodiment of the present invention, as shown in FIG. 6, during an interval in which a discharge current is uniformly maintained, namely, during the first reference time T1, operation is performed in the constant voltage output mode by controlling a constant voltage, and from a point in time at which the interval terminates to a point in time at which the reference frame terminates, namely, during the second reference time T2, an operation is made in the constant current output mode by controlling a constant current.

For example, in order to continuously maintain the current value of the constant voltage output mode in the constant current output mode, the constant current pulse wave generating apparatus 100 generates a reference current value Ir for controlling a constant current and controls the DC/DC converter 2 to continuously perform a constant current controlling operation after the first reference time T1, whereby a uniform discharge current as shown in FIG. 6 can be maintained during the discharge operation period of the reference frame (e.g., one frame).

The output voltage detection unit 7 may perform a function of detection an output voltage of the DC/DC converter 2. The output voltage detection unit 7 may include resistors R27 and R59.

The constant voltage output controller 8 of the controller 50 may operate during a period starting from a point in time at which the reference frame starts to a point in time when a signal applied from the first switching unit 10 is received, namely, during the first reference time T1. The constant voltage output controller 8 may compare an output voltage of the DC/DC converter 2 detected by the output voltage detection unit 7 and a reference voltage value Vr used for controlling a constant voltage, which is set by a reference voltage value Vr input terminal (a fifth terminal), and output a constant voltage output control signal to the DC/DC converter 2 based on the comparison voltage value to allow the DC/DC converter 2 to output a constant voltage. In order to perform such a function, the constant voltage output controller 8 may include a comparator U3:A, a photocoupler PC6, a transistor Q22, a resistor R60, and the like.

The first switching unit 10 may turn off the operation of the constant voltage output controller 8 by outputting an operation OFF signal to the constant voltage output controller 8 at a point in time when the first reference time T1 arrives. The first switching unit 10 may be comprised of, for example, a 1 mS pulse generator 10-1, and the like. Reference numeral U7:F denotes a phase inverter and C63 denotes a capacitor used for inputting a signal.

The output current detection unit 5 may detect a current introduced to the flash lamp L after being output from the DC/DC converter 2. In order to perform such a function, the output current detection unit 5 may include, for example, a resistor R90, or the like.

The reference current value generation unit 4 may store the current value detected by the output current detection unit 5 during the first reference time T1, as a reference current value Ir used for controlling a constant current therein (e.g., store through charging). The reference current value generation unit 4 may be comprised of, for example, a transistor Q10, a condenser C54, a resistor R212, and the like.

The constant current output controller 3 of the controller 50 may operate during the second reference time T2, namely, from the first reference time T1 to a point in time at which the reference frame terminates (at a point in time at which one frame terminates, e.g., 330 mS). The constant current output controller 3 may compare the output current of the DC/DC converter 2 detected by the output current detection unit 5 and the reference current value Ir used for controlling a constant current output from the reference current value generation unit 4, and output a constant current output control signal to the DC/DC converter 2 based on the comparison value to allow the DC/DC converter 2 to output a constant current.

Thus, the constant voltage output mode is performed until the first reference time T1, and the constant current output mode may be performed from the first reference time T1 to the point in time at which the reference frame terminates (T1+T2).

The constant current output controller 3 may include, for example, a comparator U4:A, a resistor R72, a photocoupler PC10, a transistor Q23, a photocoupler PC9, a resistor R74, a diode D1, a diode D2, and the like.

The second switching unit 9 may perform a function of controlling the constant current output controller 3 to be turned on during the second reference time T2, namely, from the first reference time T1 to the reference frame termination timing (one frame termination timing). The second switching unit 9 may include an amplifier (U5:E) outputting 329 mS pulse, diodes D3 and D4, and the like.

Meanwhile, when the discharging operation of the reference frame terminates, the third switching unit 14 may output a driving control signal indicating extinction of the reference current value Ir used for controlling a constant current to the reference current value generation unit 4. The third switching unit 14 may include a 5 mS pulse generator 14-1, a capacitor C82 used for inputting a signal, and the like.

Thus, when the discharging operation of the reference frame terminates, the reference current value generation unit 4 may extinguish the reference current value Ir used for controlling a constant current, stored therein according to controlling of the operation of the third switching unit 14. And then, when a next discharge frame starts, the reference current value generation unit 4 may store a new reference current value Ir used for controlling a constant current. Thus, the reference current value Ir used for controlling a constant current may be updated for every reference frame.

The reference frame timer 23 may perform a function of outputting a control signal for operating the third switching unit 14 to the third switching unit 14 at a point in time at which the reference frame (e.g., 330 mS) terminates. The reference frame timer 23 may include a one frame (330 mS) pulse generator 23-1, a capacitor C66, and the like.

The converter ON/OFF controller 13 may turn on the DC/DC converter 2 by a ready-in signal input to a signal input unit CN1 to charge the DC/DC converter 2, e.g., specifically, an output smoothing condenser C11 provided in the DC/DC converter 2, by an intended constant voltage output voltage, control an ON/OFF operation of the DC/DC converter by a pumping pulse input to a pumping pulse input terminal of the signal input unit CN1, and turn on the DC/DC converter 2 during a pulse period and turn off the DC/DC converter 2 during a pulse idle period in case of a pumping operation by divided pulses. The converter ON/OFF controller 13 may include a transistor Q12, resistors R67 and R74, and the like.

In order for the output smoothing condenser C11, provided in the DC/DC converter 2, to be constantly charged and maintain a voltage having a level sufficient to allow a pumping current of a constant current to flow even when the DC/DC converter 2 is turned off, the output pulse switch unit 17 is connected to an output terminal 26 and synchronized with a pumping pulse input to perform an ON/OFF operation. Thus, although the DC/DC converter 2 stops its operation, the charged voltage of the output smoothing condenser C11 is not discharged but the voltage just before the DC/DC converter 2 stops its operation can be maintained.

In this case, although the DC/DC converter 2 is in an OFF state, the output smoothing condenser c11 is constantly charged with a voltage having a level sufficiently allowing a pumping current of a constant current to flow.

The reason is because the output pulse switch 17 is synchronized with the pumping pulse and performs ON/OFF operation in a pumping output line, so the charged voltage of the output smoothing condenser C11 is not discharged although the DC/DC converter 2 stops its operation and the voltage just before the DC/DC converter 2 stops its operation is maintained in the output smoothing condenser C11. Thus, for this reason, a rising speed of the pumping pulse output current (voltage) can be increased. In addition, a falling speed can also be increased by turning off the output pulse switch 17.

If the DC/DC converter 2 is controlled by controlling only the constant current without controlling the constant voltage at an initial stage 1 mS of pumping, an initial rising time of the pumping pulse would be greatly lengthened. The output pulse switch 17 may include a switching element Q100, an amplifier (U5:A), a resistor R34, a photocoupler PC1, a transistor Q7, a resistor R210, and the like.

The reverse pulse removing unit 15 is configured to remove a reverse impulse voltage generated as soon as the output pulse switch 17 is turned off. The reverse pulse removing unit 15 may be configured through a diode D29, or the like.

The simmer back flow preventing unit 18 may perform a function of preventing a simmer current (voltage), which is being supplied to both ends of the flash lamp through output terminals 25 and 26, from flowing backward to the DC/DC converter 2. The simmer back flow preventing unit 18 may be configured by insertedly installing, for example, a diode D35.

The output line regulating units 16 and 19 may refer to switching elements for interrupting a high trigger voltage applied to the flash lamp L so as to be fired (ignited?) into a simmer state, and then changed into an ON state. The output line regulating units 16 and 19 may include, for example, a relay switch, or the like.

When a power source of the apparatus is turned off, the residual electric charge discharge unit 21 may perform a function of discharging a voltage (electric charges) remaining in the discharge energy charge unit 1 and the output smoothing condenser C11. The residual electric charge discharge unit 21 may be comprised of transistors Q25 and Q26, a diode D5, resistors R94 and R95, a discharge resistor CN2, a condenser C80, and the like.

Here, the discharge resistor CN2 is shown to be present only in the output voltage discharge unit 20, but in actuality, as shown in the circuit illustrated in FIG. 4, the discharge resistor CN2 is an element commonly connected to both of the output voltage discharge unit 20 and the residual electric charge discharge unit 21.

The output voltage discharge unit 20 serves to discharge the voltage of the output smoothing condenser C11 which has charged the output voltage of the DC to DC converter 24. The operation of the output voltage discharge unit 20 is required to be performed in the following situation. That is, in a state in which the user sets an energy level (reference value Vr) once through a reference voltage value input terminal (a fifth terminal) of the signal input unit CN1, when the user selects a lower level reference voltage value Vr without discharging energy, the output voltage discharge unit 20 performs discharging up to an output voltage required by the low energy level set again in order to prevent a possibility of discharging excessive energy.

In order to perform such a function, the output voltage discharge unit 20 may be configured through photocouplers PC8 and PC11, diodes D8 and D425, a condenser C72 and a discharge resistor CN2, transistors Q24 and Q16, resistors R1 and R31, and the like.

The DC to DC converter 24 may refer to an element which generates DC power sources E1, E2, and E3 insulated from a ground GND.

The reference voltage floating conversion unit 22 may refer to an element converts a reference voltage value Vr input to a reference voltage value input terminal (the fifth terminal) of the signal conversion unit CN1 upon being referenced to a ground GND, while maintaining the same voltage value, and transmits the same to the constant voltage output controller 8 floating from the ground, so that the constant voltage output controller 8 can compare it with an output voltage of the DC/DC converter 2 to perform a constant voltage output controlling operation. The reference voltage floating conversion unit 22 may include amplifiers (U2:A and U2:B), photocouplers PC4 and PC3, a variable resistor VR3, resistors R21, R12, R16, R17, and R18, and the like.

Meanwhile, in the constant current pulse wave generating apparatus according to an embodiment of the present invention, when the discharging operation is completed during the reference frame, the output smoothing condenser C11 within the DC/DC converter 2 is required to be additionally charged again, and in this case, in order to reduce the burden of the switching element Q1 within the DC/DC converter 2, the PWM controller 2-1 within the DC/DC converter 2 may perform a soft start operation. The soft start controller 11 may control such a soft start operation.

The soft start controller 11 initially electric charges the discharge energy charge unit 1 and the output smoothing condenser C11 of the DC/DC converter 2 in the ready-in stage, and in this case, the soft start controller 11 may provide control to perform soft start. The soft start controller 11 may include resistors R62, R63, R88, R87, R89, R96, and R73, transistors Q17, Q27, and Q28, a diode D6, a condenser C7, and the like.

Figure 7:
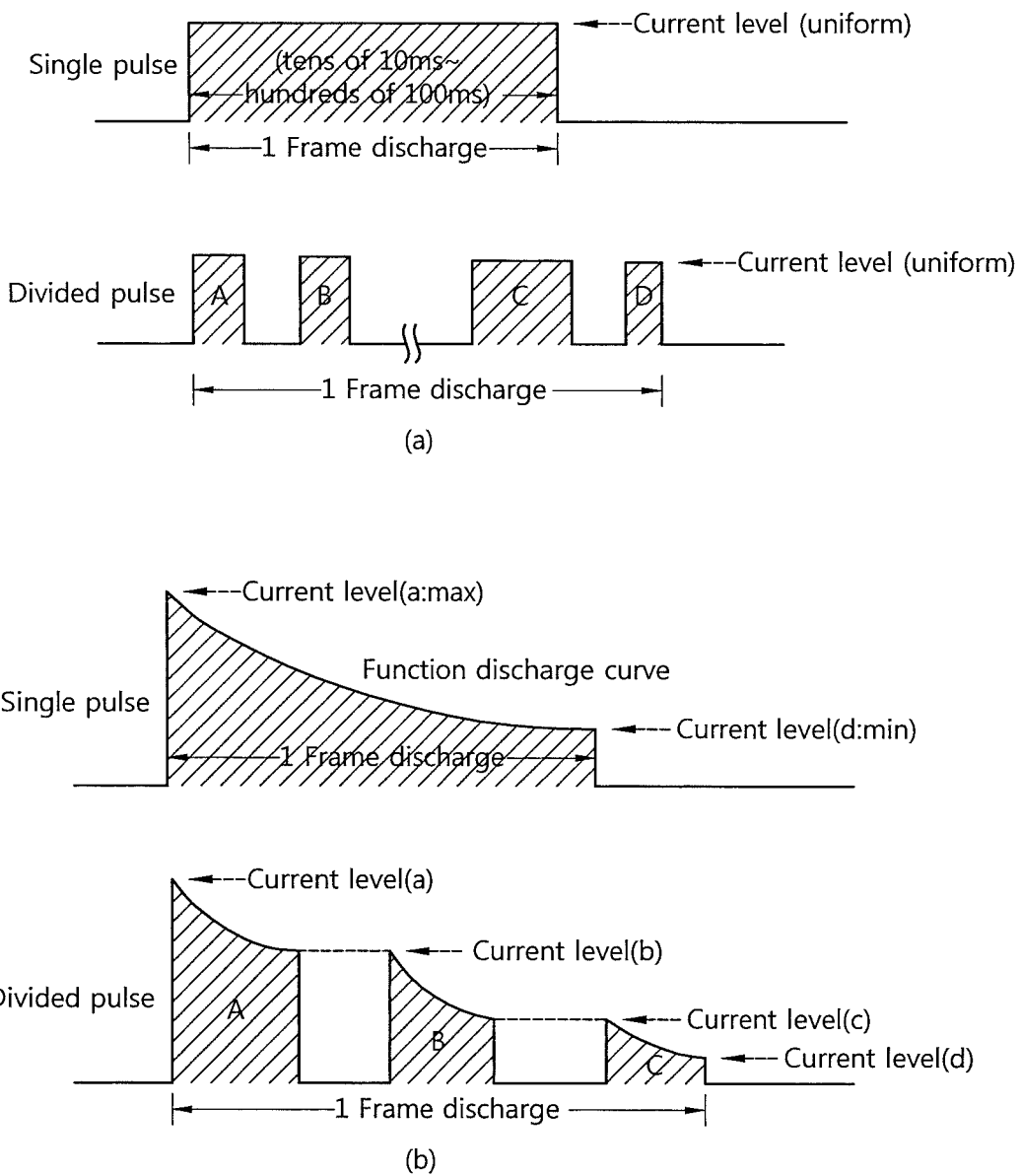
FIG. 7 is a graph sowing comparison between a current waveform of a flash lamp implemented by the apparatus for generating a constant current pulse wave according to an embodiment of the present invention and a current waveform of a flash lamp according to the related art.

FIG. 7 is a graph showing a comparison between a current waveform of a flash lamp implemented by the apparatus for generating a constant current pulse wave according to an embodiment of the present invention and a current waveform of a flash lamp according to the related art.

With reference to FIG. 7, a pumping pulse may be a single wave (single pulse) or may be a combination in the form of several divided pulse waves, i.e., a plurality of divided pulses, during the reference frame (e.g., one frame) and in this case, a slight soft start operation function is required to be granted. The first pumping pulse excluding timer 1 performs constant voltage control operation at a start portion of the single pulse or a first pumping pulse of the plurality of divided pulses in order to prevent an occurrence of an overshoot spike during a rising period of each pulse during the reference frame including single pulse or a plurality of divided pulses, so an application of the soft start function for a constant current controlling may be excluded.

The first pumping pulse excluding timer 12 may include a 330 mS pulse generator 12-1 outputting pulses during 330 mS starting from a point in time at which the first pumping pulse terminates, a signal inputting capacitor C77, and the like.

Meanwhile, the abnormal voltage detection unit 6 may detect an abnormal voltage of the DC/DC converter 2. The abnormal voltage detection unit 6 may be configured by using a comparator (U3:8), resistors R55, R58, and R30, and the like.

A pumping pulse control input signal may input to a third terminal of the signal input unit CN1. Also, the reference voltage value Vr used for controlling a constant voltage may be input to the fifth terminal in order to set an energy level, e.g., a constant current value, output to the flash lamp L. Here, the reference voltage value Vr input to the fifth terminal may be set by a user from outside.

Also, 12V may be input recognizing power ON/OFF is input to a sixth terminal and a ninth terminal of the signal input unit CN1, and a ready-in signal may be input to a seventh terminal. 15V as a circuit operation voltage Vcc may be input to a tenth terminal.

The elements of the constant current pulse wave generating apparatus according to an embodiment of the present invention have been described. Hereinafter, a driving mechanism of the constant current pulse wave generating apparatus in the aspect of a circuitry will be described.

DC charging power may charge the energy charging capacitor C1 through a charge input terminal TM1. Here, the charge energy may be $\frac{1}{2}CV^2$ (here, C is electric capacity and V is discharge voltage). A discharging operation of one frame as a reference frame is executed by the charge energy, a charge time is set and charging is performed again, and thereafter, a lamp discharging operation of a next frame is repeatedly executed.

The energy charging capacitor C1 may use tens of thousands to hundreds of thousands of uF, and may use hundreds of volts to thousands of volts as a charge voltage. This voltage performs high speed (e.g., tens of KHz) switching operation by the switching element Q1 and performs PWM (Pulse Width Modulation) operation upon receiving feedback of an output voltage (or current) by the PWM controller 2-1, and it performs energy conversion operation by a free wheel, a diode D15, and an inductor L1 and outputs a DC output voltage to the output smoothing condenser C11.

Based on a comparison between the output voltage of the DC/DCC converter 2 detected by the resistors R27 and R59 and the reference voltage value Vr input to the fifth terminal of the signal input unit CN1, the constant voltage output controller 8 controls the PWM controller 2-1 to execute a constant voltage output mode, and as mentioned above, the constant voltage output controller 8 operates only during the first reference time, e.g., 1 mS, after initiating pumping.

The PWM controller 201 operates in a constant current output mode after the 1 mS, and during 1 mS, the PWM controller 2-1 stores (i.e., electric charges) a current value detected by the resistor R90 in the condenser C54, and after the 1 mS, the PWM controller 2-1 performs a comparison and controlling operation on current values flowing in real time. A comparator (UR:A), the resistor R72, the photocoupler PC10, the transistor Q23, and the like, performs such operation to control the PWM controller 2-1 to allow a uniform output current to constantly flow.

An output signal of the 1 mS pulse generator 10-1, operates the transistor Q10 during 1 mS at an initial stage of pumping through the diode D2, the resistor R75, and the photocoupler PC9. Also, an output signal of the 5 mS pulse generator 14-1 operates the transistor Q10 through the diode D1 in the same manner, but in this case, immediately after the pumping operation of one frame is completed (in this embodiment, after 330 mS after the pumping starts), the transistor Q10 is reversibly operated for 5 mS to extinguish an output current storage signal stored in the condenser C54. This is to newly update the energy level (current level) in a next pumping operation.

The transistor Q22 of the constant voltage output controller 8 and the transistor Q23 of the constant current output controller 3 alternately operate (namely, the transistor Q22 operates for the initial 1 mS of the pumping period of one frame and the transistor Q23 operates for the subsequent period (1 mS to one frame) to change the constant voltage output mode to the constant current output mode.

To this end, a one frame pulse signal (330 mS in this embodiment) which has passed through the diode D3 after being phase-inverted from the amplifier (U7:F) and a pulse signal of one frame (330 mS-1 mS, namely, 329 mS (in case of an embodiment of the present invention) generated by mixing an output from the 1 mS pulse generator 10-1 with a signal which has passed through the diode D4 turn on the transistor Q23 to operate it in the constant current output mode.

A switching element Q100 of the output pulse switch 17 performs an ON/OFF operation on an output current, which has been constant-current controlled, by the amplifier (U5: A), the resistor R34, the photocoupler PC1, and the transistor Q7 according to a pumping pulse control input signal input to the third terminal of the signal input unit CN1 to arbitrarily control a pumping current pulse by a single wave or a plurality of pulse voltages.

The diode D29 serves to prevent a reverse pulse generated when the switch Q100 is turned off, and since the flash lamp is connected to pumping current output terminals TM2 and TM4, the diode D35 serves to a simmer current for maintaining ignition of the flash lamp from flowing backward.

As mentioned above, the amplifier (U2:A and U2:B), the photocouplers PC4 and PC3, the variable resistor VR3, the resistors R21, R12, R16, R17, and R18, and the like, are circuits for perform DC-to-DC conversion on the reference voltage value Vr input through the reference voltage value input terminal (the fifth terminal) of the signal input unit CN1 into the floating circuit region (i.e., the constant voltage output controller 8).

As mentioned above, the photocouplers PC8 and PC11, the diodes D8 and D425, the condenser C72 and the discharge resistor CN2, the transistors Q24 and Q16, the resistors R1 and R31, and the like, serve to discharge excessive energy charged in the output smoothing condenser C11 to a required level when the user updates and sets a pumping energy (voltage, current) level (in particular, when the user updates and sets to low level energy).

The transistors Q25 and Q26, the diode D5, the resistors R94 and R95, the condenser C80, and the like, serve to discharge and extinguish remaining electric charges charged in the energy charging capacitor C1, the output smoothing condenser C11, and the like, after power thereof is turned off by a 12 V input (e.g., the sixth terminal and the ninth terminal of the signal input unit CN1).

The resistors R62, R63, R88, R87, R96, and R73, the transistors Q17, Q27, and Q28, the diode D6, the condenser C7, and the like, are circuits configured to enable the PWM controller 2-1 to perform a soft start operation, and the transistor Q12 and the resistors R67 and R74 are circuits for controlling an ON/OFF operation of the PWM controller 2-1.

When a ready-in signal is input through the resistor 67, the PWM controller 2-1 is turned on, and the PWM controller 2-1 operates to be turned on only during a period in which there is a pumping pulse input during the one frame period by the transistor Q12.

Another 330 mS pulse generator 12-1 controls the transistor Q28 by outputting pulses for 330 mS starting from a point in time at which the first pumping pulse terminates, to provide a soft start operation at an initial stage of pulse rising from a second pumping pulse.

Hereinafter, a method for generating a constant current pulse wave based on the constant current pulse wave generating apparatus according to an embodiment of the present invention will be described with reference to FIGS. 3 to 8.

Figure 8:
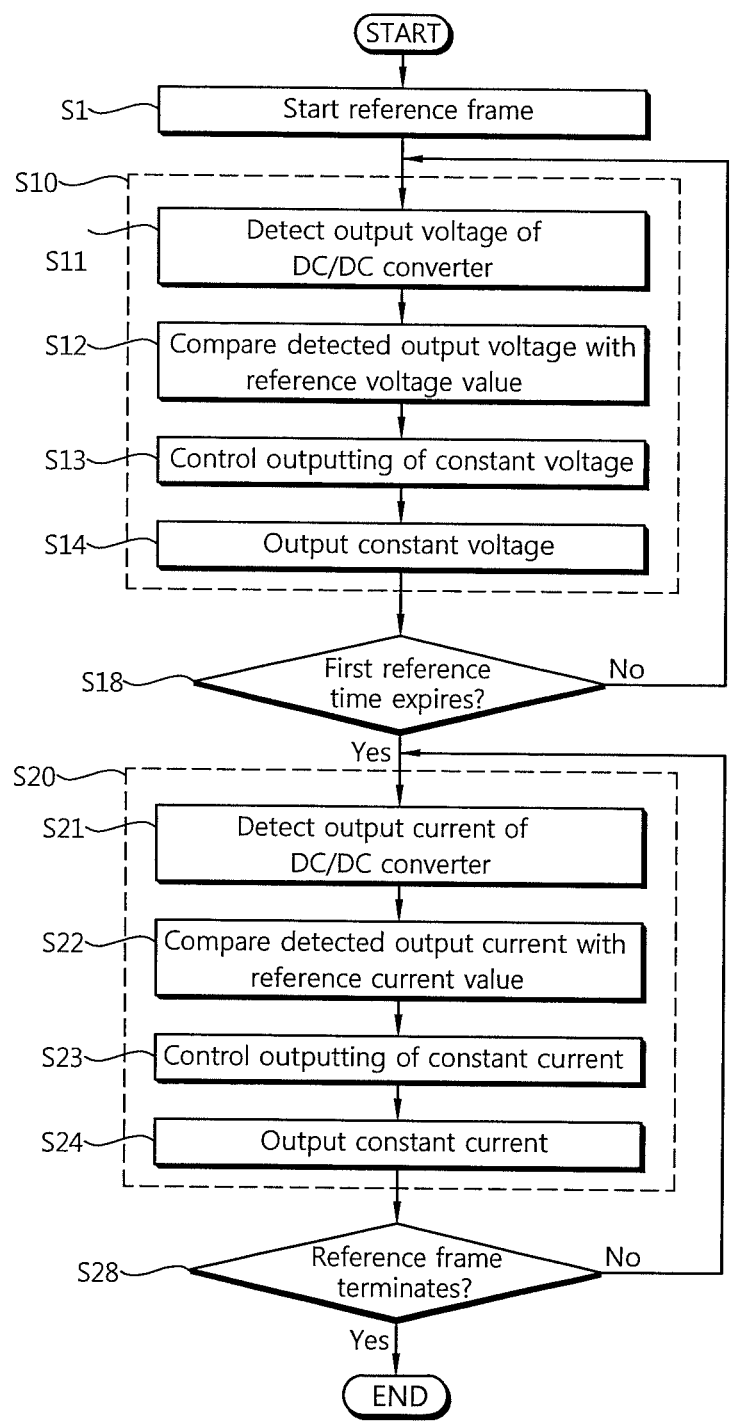
FIG. 8 is a flow chart illustrating a process of a method for generating a constant current pulse wave according to an embodiment of the present invention.

FIG. 8 is a flow chart illustrating a process of a method for generating a constant current pulse wave according to an embodiment of the present invention. Specifically, FIG. 8 shows a major operation flow of the constant current pulse wave generating apparatus during a period of a reference frame, e.g., one frame.

As shown in FIG. 8, when a reference frame starts in a state in which electric charges more than a reference level are charged in the discharge energy charge unit 1 (step S1), the constant current pulse wave generating apparatus 100 may operate in the constant voltage output mode up to a point in time at which the first reference time T1 arrives (step S10).

In the constant voltage output mode (step S10), the output voltage detection unit 7 detects an output voltage of the DC/DC converter 2 (step S11). The constant voltage output controller 8 of the controller 50 may compare an output voltage of the DC/DC converter 2 detected by the output voltage detection unit 7 and the reference voltage value Vr used for controlling a constant voltage, input through the reference voltage value Vr input terminal (the fifth terminal) of the signal input unit CN1 (step S12).

Subsequently, the constant voltage output controller 8 may perform constant voltage output controlling based on the comparison (step S13). Namely, the controller 50 operates in the constant voltage control mode. For example, the constant voltage output controller 8 may output a constant voltage output control signal allowing the DC/DC converter 2 to output a constant voltage, to the DC/DC converter 2 based on the comparison voltage value. Then, the DC/DC converter 2 may output a constant voltage to the flash lamp according to the constant voltage output control signal by using electric charges discharged from the discharge energy charge unit 1 (step S14).

Meanwhile, when the first reference time T1 expires (step S18), the constant current pulse wave generating apparatus 100 terminates the constant voltage output mode, is changed into a constant current output mode, and operates in the constant current output mode during the second reference time T2 (step S20). As mentioned above, the second reference time T2 may refer to a period of time from the first reference time to a reference frame termination time (i.e., T1+T2).

For example, the first switching unit 10 may output an operation OFF signal to the constant voltage output controller 8 at a point in time at which the first reference time T1 expires. Then, the constant voltage output controller 8 terminates an operation. Meanwhile, the second switching unit may output an operation ON signal for controlling the constant current output controller 3 to be turned on during the second reference time T2, namely, from the first reference time T1 to the reference frame termination timing (first frame termination timing), to the constant current output controller 3. Then, the controller 50 may operate in the constant current control mode during the second reference time T2.

The output current detection unit 5 may detect a current output from the DC/DC converter 2, and the reference current value generation unit 4 may store the current value detected by the output current detection unit 5 during the first reference time T1, as a reference current value Ir used for controlling a constant current therein through, for example, charging.

In the constant current output mode (step S20), the output current detection unit 5 detects a current output current of the DC/DC converter 2 (step S21). The constant current output controller 3 of the controller 50 may compare the output current of the DC/DC converter 2 detected by the output current detection unit 5 and the reference current value Ir used for controlling a constant current, output from the reference current value generation unit 4 (step S22).

Subsequently, the constant current output controller 3 may perform constant current output controlling based on the comparison (step S23). Namely, the controller 50 operates in the constant current control mode. For example, the constant current output controller 3 may output a constant current output control signal for allowing the DC/DC converter 2 to output a constant current, to the DC/DC converter 2 based on the comparison current value. Then, the DC/DC converter 2 may output a constant current to the flash lamp according to the constant current output control signal by using electric charges discharged from the discharge energy charge unit 1 (step S24).

Meanwhile, after expiration of the first reference time, when a point in time at which the second reference time expires, namely, when a point in time at which the frame terminates arrives (step S28), the constant current output mode of the constant current pulse wave generating apparatus 100 may terminate. For example, when the reference frame termination timing arrives, the second switching unit may turn off the constant current output controller 3.

At this time, the reference current value Ir used for controlling a constant current, stored in the reference current value generation unit 4 may be extinguished by controlling an operation of the third switching unit 14. And, when a next discharge frame starts, the reference current value generation unit 4 may store a new reference current value Ir used for controlling a constant current. Thus, the reference current value Ir used for controlling a constant current can be updated for each reference frame.

As described above, according to the apparatus and method for generating a constant current pulse wave according to embodiments of the present invention, energy of a constant current can be supplied to the flash lamp during the reference frame. Thus, the flash lamp can continuously generate optical energy having a uniform intensity during the reference frame, and laser light, or the like, generated based on the optical energy of the flash lamp can be stably irradiated to the affected part, e.g., the skin of a patient, and the like. Thus, a side effect, a reduction in a treatment effect, or the like, due to such a problem of irradiation of an excessive or small amount of laser light, and the like, as in the related art can be resolved, and an enhanced treatment effect can be provided.

Figure 9:
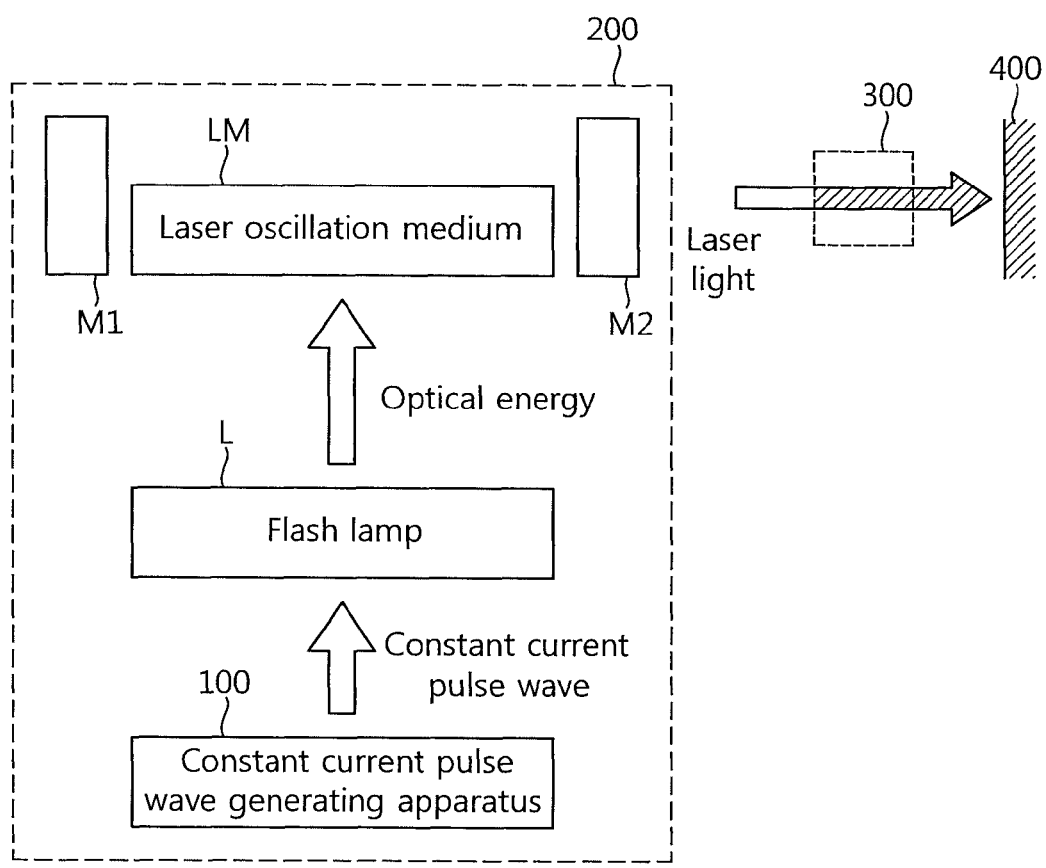
FIG. 9 is a view showing a concept of an operation for treating the affected part by using a laser generating device having the apparatus for generating a constant current pulse wave according to an embodiment of the present invention.

FIG. 9 is a view showing a concept of an operation for treating the affected part by using a laser generating device having the apparatus for generating a constant current pulse wave according to an embodiment of the present invention.

As shown in FIG. 9, a laser generating device 200 may include the constant current pulse wave generating device 100. The constant current pulse wave generating device 100 outputs a constant current having a uniform strength as shown in the graph of FIG. 6 to the flash lamp L during a reference frame.

Accordingly, the flash lamp L can continuously generate optical energy having a uniform intensity by using the constant current output from the constant current pulse wave generating device 100. Then, a laser oscillation terminal including a laser generating medium LM, a reflective plate M1, a translucent reflective plate M2, and the like, may generate laser light of a particular wavelength from light excited from the laser generating medium LM. The laser generating medium LM may be Nd:YAG, Ruby, $CO_2$, He, Ne, or the like.

Then, the laser light generated from the laser generating device may irradiate laser light for a treatment to the affected part 400, e.g., the patient's skin, or the like, through an affected part irradiation hand piece 300, such as a hand piece for treating a skin, or the like. In this case, the laser light, and the like, generated based on optical energy of the flash lamp is uniformly and stably irradiated to the affected part, e.g., the patient's skin, or the like, an enhanced treatment effect can be provided.

While the present invention has been shown and described in connection with the embodiments, it will be apparent to those skilled in the art that modifications and variations can be made without departing from the spirit and scope of the invention as defined by the appended claims.

The invention claimed is:

1. An apparatus for generating a constant current pulse wave, the apparatus comprising:
a charge unit receiving a current and charging electric charges;
a converter unit applying a constant voltage to a flash lamp during a first reference time and applying a constant current to the flash lamp during a second reference time by using the electric charges charged in the charge unit; and
a controller operating in a constant voltage control mode to transmit a constant voltage control signal for controlling the converter unit to output the constant voltage, to the converter unit during the first reference time and operating in a constant current control mode to transmit a constant current control signal for controlling the converter unit to output the constant current, to the converter unit during the second reference time;
an output voltage detection unit detecting an output voltage of the converter unit; and an output current detection unit detecting a current output from the converter unit, wherein the controller comprises a constant voltage output controller operating during the first reference time, comparing the output voltage of the converter unit detected by the output voltage detection unit with a pre-set reference voltage value used for controlling a constant voltage, and outputting a constant voltage output control signal for controlling the converter unit to output the constant voltage to the converter unit based on the comparison voltage value; and wherein a constant current output controller operating during the second reference time, comparing the output current of the converter unit detected by the output current detection unit with a pre-set reference current value used for controlling a constant current, and outputting a constant current output control signal for controlling the converter unit to output the constant current to the converter unit based on the comparison current value.

2. The apparatus for generating a constant current pulse wave of claim 1, wherein the second reference time is a period of time until a point in time at which as reference frame terminates after the first reference time expires.

3. The apparatus for generating a constant current pulse wave of claim 1, further comprising:
a reference current value generation unit storing the current value detected by the output current detection unit during the first reference time, as the reference current value used for controlling a constant current.

4. The apparatus for generating a constant current pulse wave of claim 3, wherein when the reference frame terminates, the reference current value generation unit extinguishes the stored reference current value used for controlling a constant current.

5. The apparatus for generating a constant current pulse wave of claim 4, further comprising:
a third switching unit outputting a signal for controlling the reference current value generation unit to extinguish the stored reference current value used for controlling a constant current, to the current value generation unit, when the reference frame terminates; and
a reference frame tinier outputting a control signal for operating the third switching unit at a point in time at which the reference frame terminates, to the third switching unit.

6. The apparatus for generating a constant current pulse wave of claim 1, further comprising:
a first switching unit outputting a signal for turning off an operation of the constant voltage output controller to the constant voltage output controller when the first reference time expires; and
a second switching unit outputting a signal for turning on an operation of the constant current output controller during the second reference time, to the constant current output controller.

7. The apparatus for generating a constant current pulse wave of claim 1, further comprising:
a converter ON/OFF controller turning on the converter unit by a read-in signal input to a signal input unit to charge the converter unit with a constant voltage output voltage, controlling an ON/OFF operation of the converter unit by a pumping pulse input to a pumping pulse input terminal of the signal input unit, turning on the converter unit during a pulse period in case of a pumping operation by divided pulses, and turning off the converter unit during a pulse idle period; and an output pulse switch unit connected to an output terminal and synchronized with a pumping pulse input to perform an ON/OFF operation to allow a voltage of an energy level sufficient to allow a pumping current of a constant current to flow in an output smoothing condenser provided in the converter unit even when the converter unit is in an OFF state.

8. The apparatus for generating a constant current pulse wave of claim 1, further comprising:
a reverse pulse removing unit removing a reverse impulse voltage generated as soon as an output pulse switch is turned off;
a simmer back flow preventing unit preventing a simmer current, which is being supplied to both ends of the flash lamp, from flowing backward;
an output line regulating unit interrupting a high trigger voltage applied to the flash lamp so as to be ignited into a simmer state, and changing it into an ON state;
a residual electric charge discharge unit discharging electric charges remaining in a discharge energy charge unit and the output smoothing condenser provided in the converter unit when the supply power is turned off;
an output voltage discharge unit discharging a voltage of the output smoothing condenser provided in the converter unit to reach an output voltage required by a low level set again in order to prevent generation of a possibility of discharging excessive energy when a low level value is selected without discharging energy after an energy level is set; and
a reference voltage floating conversion unit performing DC conversion on a reference voltage value input to a reference voltage value input terminal of a signal conversion unit after being referenced to a ground and outputting the same to the controller to allow the controller to compare the reference voltage value with an output voltage of the converter unit to perform constant voltage output controlling.

9. An apparatus for generating a constant current pulse wave, the apparatus comprising:
a charge unit receiving a current and charging electric charges;
a converter unit applying a constant voltage to a flash lamp during a first reference time and applying a constant current to the flash lamp during a second reference time by using the electric charges charged in the charge unit;
a constant voltage output controller detection an output voltage of the converter unit and applying a constant voltage control signal for controlling the converter unit to output the constant voltage, to the converter unit based on the detected output voltage and a pre-set reference voltage; and
a constant current output controller detection an output current of the converter unit and applying a constant current control signal for controlling the converter unit to output the constant current, to the converter unit based on the detected output current and a pre-set reference current.

10. The apparatus for generating a constant current pulse wave of claim 9, further comprising:
an output voltage detection unit detection an output voltage of the converter unit;
a reference current value generation unit storing the current value detected by the output current detection unit during the first reference time, as a reference current value used for controlling a constant current; and
an output current detection unit detection a current output from the converter unit.

11. The apparatus for generating a constant current pulse wave of claim 10, wherein the constant voltage output controller compares the output voltage of the converter unit detected by the output voltage detection unit with a pre-set reference voltage value used for controlling a constant voltage, and outputs a constant voltage output control signal for controlling the converter unit to output the constant voltage, to the converter unit based on the comparison voltage value, and the constant current output controller compares the output current of the converter unit detected by the output current detection unit with a reference current value used for controlling the constant current, and outputs a constant current output control signal for controlling the converter unit to output the constant current, to the converter unit based on the comparison current value.

12. A method for generating a constant current pulse wave using an apparatus for generating a constant current pulse wave, the method comprising:

receiving a current and storing electric charges in a charge unit;

performing a constant voltage output mode to perform constant voltage controlling by using the stored electric charges and output a constant voltage to a flash lamp during a first reference time; and performing a constant current output mode to perform constant current controlling by using the stored electric charges to output a constant current to the flash lamp during a second reference time until when a reference frame terminates after the first reference time expires, wherein the performing of the constant voltage output mode comprises:

detecting an output voltage of it converter unit;

comparing the detected output voltage of the converter unit with a pre-set reference voltage value to calculate a comparison voltage value; and controlling the converter unit to output the constant voltage, based on the comparison voltage value.

13. The method of claim 12, wherein the performing of the constant current output mode comprises:

detection an output current of the converter unit;

comparing the detected output current of the converter unit with a predetermined reference current value to calculate a comparison current value; and controlling the converter unit to output the constant current, based on the comparison current value.

14. The method of claim 13, further comprising:

detection an output current of the converter unit during the first reference time; and storing the output current of the converter unit detected during the first reference time, as a reference current value used for controlling the constant current.

15. The method of claim 14, further comprising:

extinguishing the stored reference current value used for controlling the constant current when the reference frame termination timing arrives.

* * * * *